United States Patent
Lin et al.

(10) Patent No.: US 11,566,013 B1
(45) Date of Patent: Jan. 31, 2023

(54) INHIBITING MUTANT ISOCITRATE DEHYDROGENASE 1 (MIDH1)

(71) Applicant: FORMA Therapeutics, Inc., Watertown, MA (US)

(72) Inventors: Jian Lin, Acton, MA (US); George P. Luke, Clinton, CT (US); Madhu Mondal, Winchester, MA (US)

(73) Assignee: FORMA Therapeutics, Inc., Watertown, MA (US)

(*) Notice: Subject to any disclaimer, the term of this patent is extended or adjusted under 35 U.S.C. 154(b) by 254 days.

(21) Appl. No.: 16/953,112

(22) Filed: Nov. 19, 2020

Related U.S. Application Data

(60) Provisional application No. 62/944,401, filed on Dec. 6, 2019, provisional application No. 62/937,943, filed on Nov. 20, 2019.

(51) Int. Cl.
*C07D 401/12* (2006.01)
*A61K 9/00* (2006.01)
*A61K 9/20* (2006.01)
*A61K 9/48* (2006.01)
*A61K 31/706* (2006.01)

(52) U.S. Cl.
CPC .......... *C07D 401/12* (2013.01); *A61K 9/0019* (2013.01); *A61K 9/0053* (2013.01); *A61K 9/20* (2013.01); *A61K 9/48* (2013.01); *A61K 31/706* (2013.01)

(58) Field of Classification Search
CPC .. C07D 401/12; A61K 9/0019; A61K 9/0053; A61K 9/20; A61K 9/48; A61K 31/706
USPC ......................................................... 514/335
See application file for complete search history.

(56) References Cited

FOREIGN PATENT DOCUMENTS

WO  WO-2016044789 A1 * 3/2016 .............. A61P 35/00

* cited by examiner

*Primary Examiner* — Kristin A Vajda
(74) *Attorney, Agent, or Firm* — James J. Diehl

(57) ABSTRACT

This disclosure relates to compositions and methods for inhibiting mutant IDH1, useful in treatment of mIDH1 cancers including AML, as well as mIDH1-positive solid tumors such as glioma.

20 Claims, No Drawings

INHIBITING MUTANT ISOCITRATE DEHYDROGENASE 1 (MIDH1)

RELATED APPLICATIONS

This application claims priority to U.S. Provisional Patent Appl. No. 62/937,943, filed Nov. 20, 2019, and U.S. Provisional Patent Appl. No. 62/944,401, filed Dec. 6, 2019, the entire contents of each of which are hereby incorporated by reference.

TECHNICAL FIELD

The present disclosure relates to the treatment of cancer harboring an isocitrate dehydrogenase 1 (IDH1) mutation.

BACKGROUND

Mutant IDH1 is a genetically validated target in hematologic cancers, including AML. Mutations of IDH1 present in certain cancer cells can result in a new ability of this enzyme to catalyze the NADPH-dependent reduction of α-ketoglutarate to (R)-2-hydroxyglutarate (R-2HG). R-2HG is not formed by wild-type IDH. The presence of mutations at codon 132 in IDH1 imparts a neomorphic activity to the enzyme, resulting in the production of the "oncometabolite" R-2HG, which has pleotropic roles in tumorigenesis. Excess production of 2HG has been shown to inhibit α-KG-dependent enzymes involved in epigenetic regulation, collagen synthesis, and cell signaling, thereby leading to a block in normal differentiation of progenitor cells and the subsequent development of cancer mutations in IDH1 associated with 2HG neomorphic activity, specifically R-2HG neomorphic activity, including mutations at residues 97, 100, and 132, e.g. G97D, R100Q, R132H, R132C, R132S, R132G, R132L, and R132V. IDH mutation-specific inhibitors have been shown to reduce aberrantly elevated levels of the oncometabolite R-2HG, resulting in antitumor efficacy in preclinical models.

SUMMARY

The compound (S)-5-((1-(6-chloro-2-oxo-1,2-dihydroquinolin-3-yl)ethyl)amino)-1-((methylthio)methyl)-6-oxo-1,6-dihydropyridine-2-carbonitrile (I-1) inhibits production of 2HG by mutated IDH1 (mIDH1), including both the R132C and R132H mutated IDH1 enzymes (as measured by the assays provided herein).

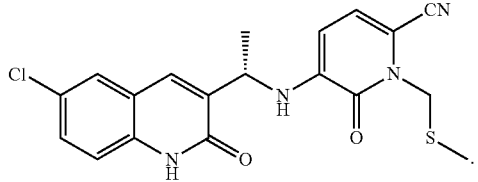

(I-1)

Compound I-1 can be combined with another mutant IDH1 inhibitor compound (S)-5-((1-(6-chloro-2-oxo-1,2-dihydroquinolin-3-yl)ethyl)amino)-1-methyl-6-oxo-1,6-dihydropyridine-2-carbonitrile (I-2):

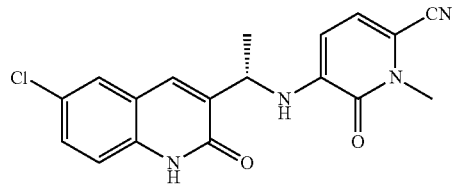

(I-2)

Another aspect of the disclosure relates to a method of treating a disease or disorder associated with mutant IDH1. The method involves administering to a patient in need of treatment for diseases or disorders associated with mutant IDH1 an effective amount of Compound I-1 or a combination of Compound I-1 and Compound I-2. In some embodiments, when a total dose of Compound I-2 of about 300 mg is administered daily (e.g., 150 mg of Compound I-2 orally administered twice per day) to a patient with Compound I-1, the total amount of Compound I-1 administered to the patient is preferably less than about 1.5 mg daily (i.e., from lowest amount detectable (e.g., by HPLC, e.g., by HPLC according to the method provided in the Examples section below) to about 1.5 mg daily). In some embodiments, the method involves administering Compound I-1 daily to a patient in need thereof (e.g., a daily total dose of Compound I-1 of from about 1.3 mg to about 22 mg, from about 1.3 mg to about 15 mg, from about 1.3 mg to about 10 mg, or from about 1.3 mg to about 5 mg in combination with 300 mg of Compound I-2). In some embodiments, the method involves administering daily to a patient in need thereof, a daily total dose of Compound I-1 ranging from a lowest amount detectable (e.g., a lower detection limit of about 0.01% detected when using the HPLC method provided in the Examples below) up to about 22 mg, from about 1.3 mg to about 15 mg, from about 1.3 mg to about 10 mg, or from about 1.3 mg to about 5 mg in combination with 300 mg of Compound I-2. In some embodiments, the method involves administering daily to a patient in need thereof, a daily total dose of Compound I-1 ranging from a lowest detectable amount (e.g., a lower detection limit of about 0.01% detected when using the HPLC method provided in the Examples below) up to about 11 mg or from about 0.65 mg to about 7.5 mg in combination with 150 mg of Compound I-2 in a dose administered twice per day (BID) to a patient in need thereof.

Compound 1-1 can be administered in a single pharmaceutical composition with Compound I-2. In some embodiments, the method involves administering daily to a patient in need thereof an Active Pharmaceutical Ingredient (API) comprising a mixture of Compound 1-1 and Compound I-2. For example, an API can comprise about 0.05-0.10% (a/a) by HPLC of Compound I-1 (e.g., using the HPLC method provided in the Examples), in addition to over 90% (including, e.g., >95%, >98%, or >99% or greater) (a/a) by HPLC of Compound I-2. The API can also comprise at least 99% (a/a) by HPLC of Compound I-2 in combination with a total of about 0.05-0.10% (a/a) by HPLC of Compound I-1 (e.g., using the HPLC method provided in the Examples).

DETAILED DESCRIPTION

Compound 1-1 can be administered to a patient in a pharmaceutical composition. Preferably, the pharmaceutical composition comprises a compound indicated for the treatment of adult patients with relapsed or refractory acute myeloid leukemia (AML) with a susceptible IDH1 mutation as detected by an FDA-approved test. The cancer patient can be diagnosed with AML characterized by the detection of IDH1 mutations in blood or bone marrow. AML patients without IDH1 mutations at diagnosis can be retested at relapse because a mutation in IDH1 may emerge during treatment and at relapse.

Compound 1-1 can be administered in an oral dosage form in combination with Compound I-2. Compound I-2 is a small molecule inhibitor that targets the mutant isocitrate dehydrogenase 1 (mIDH1) enzyme. Susceptible IDH1 mutations are defined as those leading to increased levels of 2HG in leukemia cells. The most common of such mutations are R132H and R132C substitutions. In some embodiments, Compound 1-2 can be administered in a dose of 150 mg twice per day in combination with up to about 1.3 mg of Compound I-1 per day.

Pharmaceutical compositions for treating a patient diagnosed with a cancer harboring a mIDH1 mutation (e.g., R132H or R132C) preferably include Compound I-1 combined with an amount of Compound I-2 effective to increase the inhibitory activity of Compound I-1 in the R132H and/or R132C mIDH1 enzymatic assay of Example 2. Preferably, the amount of Compound 1-1 is selected to decrease the $IC_{50}$ value in either or both of the R132H or R132C mIDH1 enzymatic assays by at least about 8%, and most preferably by at least about 10%, compared to the $IC_{50}$ value obtained using Compound 1-2 in the absence of Compound 1-1. The pharmaceutical composition preferably contains both Compound 1-2 and Compound 1-1 in a weight ratio of up to 225:1. When the administered pharmaceutical composition provides a total daily dose of 300 mg of Compound 1-2 per day to a patient in need thereof (e.g., 150 mg of Compound 1-2 administered orally twice per day), the pharmaceutical composition preferably comprises up to 1.33 mg of Compound 1-1 per 300 mg of Compound 1-2 (i.e., from smallest detectable amount by HPLC to about 1.33 mg of Compound I-1 per 300 mg of Compound 1-2). The pharmaceutical composition can contain 0.05-0.5% of Compound I-1 relative to Compound I-2 as measured by HPLC (a/a). In some embodiments, the pharmaceutical composition comprises 0.05-0.5% Compound I-1 relative to Compound 1-2 as measured by HPLC (a/a). Preferably, the pharmaceutical composition comprises up to 0.2% (a/a, HPLC) of Compound 1-1 relative to Compound I-2. In some embodiments, a pharmaceutical composition comprises an amount of Compound 1-1 selected to provide up to 0.1% (a/a, HPLC) or 1 mg of Compound 1-1 to a patient per day. For example, a pharmaceutical composition can comprise up to 0.1% (a/a, HPLC) of Compound I-1 with 300 mg of Compound 1-2. In another embodiment, a pharmaceutical composition can comprise up 1 mg of Compound I-1 per 300 mg of Compound 1-2, to be administered to a patient in need thereof having a cancer harboring an IDH-1 mutation, in two equal doses each comprising 150 mg of Compound 1-2.

The disclosure is based in part on the recognition that, surprisingly, a combination of Compound 1-1 and 1-2 was more potent against both R132H and R132C (as measured using the assay of Example 2) than the corresponding weighted average of the $IC_{50}$, values of each of Compound I-1 and Compound 1-2 alone.

Table 1 provides the $IC_{50}$ values of Compounds I-1 and 1-2 (separately and together) with IDH1-R132H and IDH1-R132C mutant enzymes using the assay described in Example 2. Compound I-1 and Compound 1-2 were highly potent (less than 80 nM) against both R132H and R132C IDH1 mutant enzymes.

TABLE 1

| Compound Number | IDH1 R132H $IC_{50}$ (nM) | IDH1 R132C $IC_{50}$ (nM) |
| --- | --- | --- |
| I-1 | 10.0 | 12.9 |
| I-2 | 14.3 | 77.0 |
| I-1 + I-2 (0.07:99.6) | 12.9 | 67.1 |

An $IC_{50}$ value of about 12.9 nM was observed in the R132H mIDH1 Enzyme Assay (Example 2) from a test sample containing Compound I-1 and Compound I-2 in a ratio of 0.07:99.6 (as measured by HPLC). Surprisingly, this value is about 10% lower (indicating unexpectedly increased activity) than the weighted average of corresponding R132H mIDH1 (Example 2) $IC_{50}$ values (i.e., 0.07% of Compound I-1 with an $IC_{50}$ value of 10 nM and 99.93% of Compound I-2 with an $IC_{50}$ value of 14.3 nM provides a weighted average of 14.3 nM).

Furthermore, an $IC_{50}$ value of about 67.1 nM was observed in the R132C mIDH1 Enzyme Assay (Example 2) from the test sample containing Compound I-1 and Compound I-2 in a ratio of 0.07:99.6 (as measured by HPLC). Surprisingly, this value is about 13% lower (indicating unexpectedly increased activity) than the weighted average of corresponding R132C mIDH1 (Example 2) $IC_{50}$ values (i.e., 0.07% of Compound I-1 with an $IC_{50}$ value of 12.9 nM and 99.93% of Compound I-2 with an $IC_{50}$ value of 77.0 nM provides a weighted average of 77.0 nM).

Optionally, Compound I-1 and/or Compound I-2 can be administered to a patient receiving azacitidine and/or cytarabine for the treatment of a hematological cancer (e.g., AML). Low dose cytarabine (LDAC) is considered a standard of care (SOC) treatment option for AML patients who are not candidates for intensive therapy. In a xenograft model, the combination of an IDH1 inhibitor with short duration low dose cytarabine decreased the bone marrow tumor burden better than either treatment alone. The azacitidine can be subcutaneously or intravenously administered to the patient in an azacitidine treatment cycle consisting of administration of a total dose of 75 mg/m$^2$ each day for 7 consecutive days beginning at the start of each treatment cycle, followed by 21 consecutive days without administration of azacitidine to the patient. A 48-hour dose interruption of azacitidine is allowed for weekends or holidays. If no response is seen after 2 treatment cycles, azacitidine can be administered at a total dose of 100 mg/m$^2$ each day.

In some embodiments, Compound I-1 is administered in a pharmaceutical composition comprising a compound indicated for the treatment of adult patients with solid tumors of the central nervous system (CNS), such as glioma, harboring an IDH1 mutation. In some embodiments, the pharmaceutical composition is administered as part of a combination therapy also comprising azacitidine.

Compound I-1 can be synthesized by following the steps outlined in Scheme 1 below. Starting materials are either commercially available or made by procedures known in the literature. Compounds 1.1 and 1.3 are known in the art and their synthesis can be found in WO2016/044789, the disclosure of which is incorporated herein by reference.

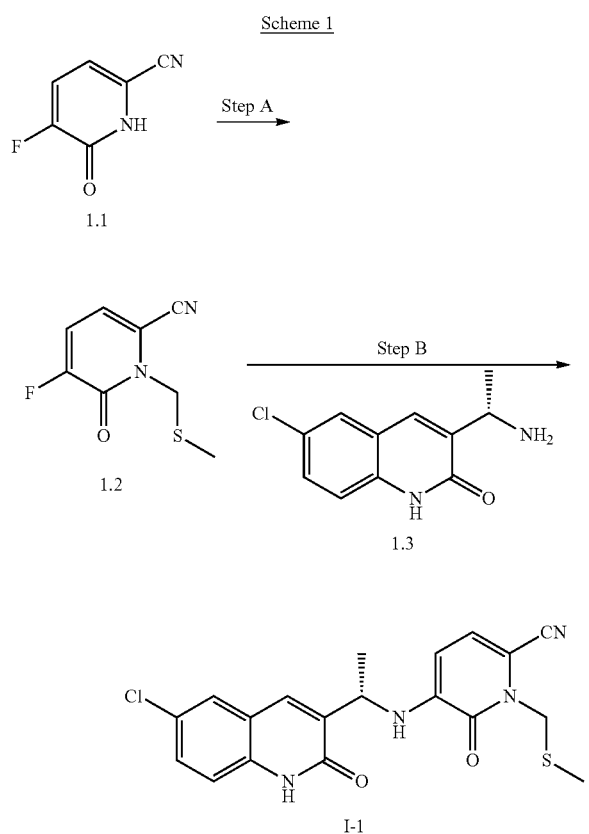 [SMILES: N#Cc1ccc(F)c(=O)[nH]1 ; CSCn1c(C#N)ccc(F)c1=O ; C[C@H](N)c1cc2cc(Cl)ccc2[nH]c1=O ; CSCn1c(C#N)ccc(N[C@@H](C)c2cc3cc(Cl)ccc3[nH]c2=O)c1=O ; [I-]]

A general route to prepare Compound 1-1 using intermediates 1.1 and 1.3 is outlined in Scheme 1. Alkylation of intermediate 1.1 under standard nucleophilic substitution conditions using a base in a polar aprotic solvent gives thioether compound 1.2 (Step A). Nucleophilic aromatic substitution of intermediate 1.3 with thioether compound 1.2 in the presence of a base in a polar aprotic solvent gives Compound 1-1 (Step B).

The synthesis of Compound I-2 is disclosed in Example 25 (as compound I-13) in publication WO2016/044789 (published Mar. 24, 2016; filed as PCT patent application PCT/US2015/051055 on Sep. 18, 2015), incorporated herein by reference. The USAN name OLUTASIDENIB has been assigned to Compound I-2 (CAS Registry 1887014-12-1), and it is also referred to as:

2-Pyridinecarbonitrile, 5-[[(1S)-1-(6-chloro-1,2-dihydro-2-oxo-3-quinolinyl)ethyl]amino]-1,6-dihydro-1-methyl-6-oxo-, or 5-{[(1S)-1-(6-chloro-2-oxo-1,2-dihydroquinolin-3-yl)ethyl]amino}-1-methyl-6-oxo-1,6-dihydropyridine-2-carbonitrile, or (S)-5-((1-(6-chloro-2-oxo-1,2-dihydroquinolin-3-yl)ethyl)amino)-1-methyl-6-oxo-1,6-dihydropyridine-2-carbonitrile.

EXEMPLARY EMBODIMENTS

The following numbered embodiments, while non-limiting, are exemplary of certain aspects of the disclosure:

1. Compound I-1 or pharmaceutically acceptable salt thereof:

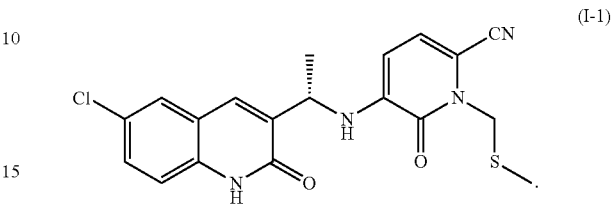

2. A pharmaceutical composition comprising the compound of embodiment 1.

3. The pharmaceutical composition of embodiment 2, further comprising Compound I-2 or a pharmaceutically acceptable salt thereof:

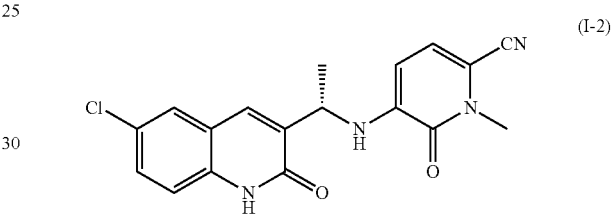

4. A method of inhibiting mutant isocitrate dehydrogenase 1 (mIDH1) comprising contacting the compound of embodiment 1 with a cell harboring an IDH1 mutation selected from the group consisting of R132H and R132C under conditions effective to inhibit the mIDH1 enzymatic activity of the cell when the mIDH1 activity is assessed using the enzymatic assay of Example 2.

5. A method of reducing the concentration of 2-hydroxyglutarate in a patient diagnosed with a cancer harboring an IDH1 mutation, the method comprising administering to the patient in need thereof the compound of embodiment 1.

6. A method of treating a patient diagnosed with acute myeloid leukemia (AML) harboring an IDH1 mutation, the method comprising administering to the patient in need thereof a therapeutically effective amount of the pharmaceutical composition of embodiment 3.

7. The method of embodiment 6, comprising administering to the patient up to about 22 mg of Compound 1-1 per day.

8. The method of embodiment 7, comprising administering to the patient a total of about 300 mg of Compound I-2 per day.

9. The method of embodiment 8, comprising administering to the patient a total of about 300 mg of Compound I-2 and up to about 1.33 mg of Compound I-1 per day.

10. The method of embodiment 9, comprising orally administering 150 mg of Compound I-2 to the patient twice a day.

11. The method of embodiment 7, comprising orally administering to the patient twice a day up to about 11 mg of Compound I-1.

12. The method of embodiment 11, comprising orally administering to the patient twice a day 150 mg of Compound I-2.

13. A pharmaceutical composition comprising (S)-5-((1-(6-chloro-2-oxo-1,2-dihydroquinolin-3-yl)ethyl)amino)-1-((methylthio)methyl)-6-oxo-1,6-dihydropyridine-2-carbonitrile.

14. The pharmaceutical composition of embodiment 13, further comprising (S)-5-((1-(6-chloro-2-oxo-1,2-dihydroquinolin-3-yl)ethyl)amino)-1-methyl-6-oxo-1,6-dihydropyridine-2-carbonitrile.

15. The pharmaceutical composition of embodiment 14, comprising a total of 0.01-0.5% (a/a HPLC) (S)-5-((1-(6-chloro-2-oxo-1,2-dihydroquinolin-3-yl)ethyl)amino)-1-((methylthio)methyl)-6-oxo-1,6-dihydropyridine-2-carbonitrile, relative to (S)-5-((1-(6-chloro-2-oxo-1,2-dihydroquinolin-3-yl)ethyl)amino)-1-methyl-6-oxo-1,6-dihydropyridine-2-carbonitrile.

16. The pharmaceutical composition of embodiment 15, comprising up to about 1.33 mg of (S)-5-((1-(6-chloro-2-oxo-1,2-dihydroquinolin-3-yl)ethyl)amino)-1-((methylthio)methyl)-6-oxo-1,6-dihydropyridine-2-carbonitrile per 300 mg of (S)-5-((1-(6-chloro-2-oxo-1,2-dihydroquinolin-3-yl)ethyl)amino)-1-methyl-6-oxo-1,6-dihydropyridine-2-carbonitrile.

17. A unit dosage form indicated for oral delivery to a patient diagnosed with AML harboring an IDH1 mutation, the unit dosage form comprising the pharmaceutical composition of embodiment 16.

18. The unit dosage form of embodiment 17, as a capsule or a tablet comprising a total of 50 mg or 150 mg of (S)-5-((1-(6-chloro-2-oxo-1,2-dihydroquinolin-3-yl)ethyl)amino)-1-methyl-6-oxo-1,6-dihydropyridine-2-carbonitrile.

19. A method of treating a patient diagnosed with AML harboring an IDH1 mutation, the method comprising administering to the patient in need thereof a total of 150 mg of (S)-5-((1-(6-chloro-2-oxo-1,2-dihydroquinolin-3-yl)ethyl)amino)-1-methyl-6-oxo-1,6-dihydropyridine-2-carbonitrile twice a day in a unit dosage form, wherein each unit dosage form further comprises (S)-5-((1-(6-chloro-2-oxo-1,2-dihydroquinolin-3-yl)ethyl)amino)-1-((methylthio)methyl)-6-oxo-1,6-dihydropyridine-2-carbonitrile in an amount of at least 0.01% a/a (HPLC) and up to 0.665 mg per unit dosage form.

EXAMPLES

Unless otherwise noted, reagents and solvents were used as received from commercial suppliers. Proton nuclear magnetic resonance (NMR) spectra were obtained on either Bruker or Varian spectrometers at 400 MHz. Spectra are given in ppm (δ) and coupling constants, J, are reported in Hertz. Tetramethylsilane (TMS) was used as an internal standard. Mass spectra were collected using a Waters ZQ Single Quad Mass Spectrometer (ion trap electrospray ionization (ESI)).

High performance liquid chromatography (HPLC) was performed on an HPLC system which included a quaternary or binary HPLC pump, variable wavelength or photo diode array UV/visible detector, data collection system, and autosampler with temperature control. Mobile Phase A: 0.05% TFA/water; Mobile Phase B: 0.05% TFA/acetonitrile. The HPLC operating conditions are summarized below:
Column Waters, XBridge C18, 4.6×150 mm, 3.5 μm
Wavelength 235 nm
Autosampler temperature ambient (not controlled)
Column temperature 35° C.
Flow rate 1.0 mL/min
Injection volume 10.0 μL

| Gradient | Time, min | % A | % B |
|---|---|---|---|
| | 0.00 | 80 | 20 |
| | 15.00 | 40 | 60 |
| | 20.00 | 10 | 90 |
| | 21.00 | 80 | 20 |
| | 30.00 | 80 | 20 |

Example 1. Synthesis of (S)-5-((1-(6-Chloro-2-oxo-1,2-dihydroquinolin-3-yl)ethyl)amino)-1-((methylthio)methyl)-6-oxo-1,6-dihydropyridine-2-carbonitrile (Compound 1-1)

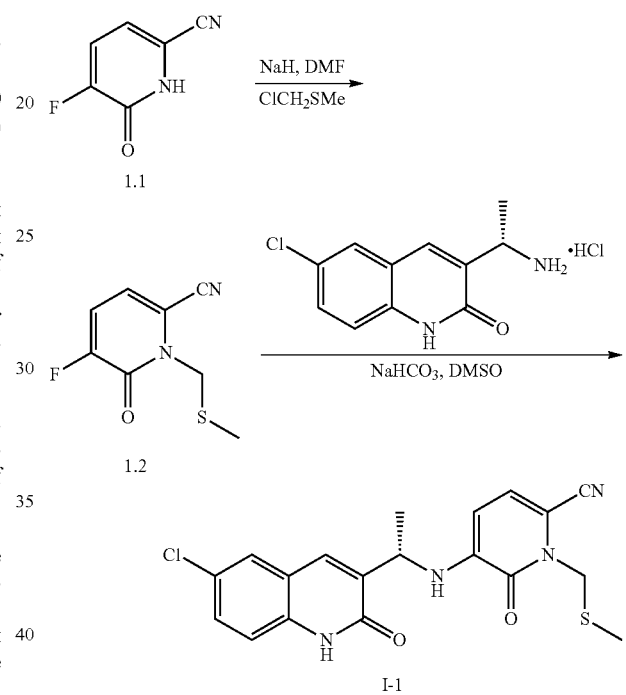

5-Fluoro-1-((methylthio)methyl)-6-oxo-1,6-dihydropyridine-2-carbonitrile (1.2). A dried, 100-mL round-bottomed flask under nitrogen was charged with 5-fluoro-6-oxo-1,6-dihydropyridine-2-carbonitrile (1.1, 500 mg, 3.62 mmol) and anhydrous DMF (15 mL). The solution was cooled in an ice bath and sodium hydride (145 mg, 3.62 mmol) was added portion-wise. The resulting mixture was stirred for 30 minutes while warming to ambient temperature. Chloromethyl methyl sulfide (0.303 mL, 3.62 mmol) was then added, followed by sodium iodide (543 mg, 3.62 mmol). The reaction mixture was stirred at ambient temperature and was monitored by $^1$H NMR. After 4 h, the reaction was quenched with saturated ammonium chloride solution. The mixture was further diluted with water and then extracted with ethyl acetate. The aqueous layer was re-extracted once with ethyl acetate, and the combined organic extracts were washed with brine, dried over sodium sulfate, and concentrated under reduced pressure. The crude product was purified by flash chromatography on silica gel, eluting with 1:4 ethyl acetate/hexanes and slowly increasing to 1:3 to produce 200 mg (28%) of 1.2 as a clear, colorless oil. $^1$H NMR (400 MHz, Methanol-$d_4$) δ ppm 7.37 (dd, J=8.98, 7.81 Hz, 1H), 7.08 (dd, J=7.81, 4.69 Hz, 1H), 5.33 (s, 2H) 2.27 (s, 3H).

(S)-5-(((1-(6-Chloro-2-oxo-1,2-dihydroquinolin-3-yl)ethyl)amino)-1-((methylthio)methyl)-6-oxo-1,6-dihydropyridine-2-carbonitrile (I-1). A 10-mL, round-bottomed flask was charged with (S)-3-(1-aminoethyl)-6-chloroquinolin-2(1H)-one hydrochloride (238 mg 0.917 mmol), DMSO (3.1 mL), 1.2 (200 mg, 1.009 mmol), and sodium bicarbonate (231 mg, 2.75 mmol). The resulting mixture was heated to 80° C. and monitored by LC/MS analysis. After 5 hours, the heating was discontinued and the reaction mixture was stirred overnight while slowly cooling to ambient temperature. LC/MS analysis indicated complete conversion. Water (2.82 mL) was added drop-wise over several minutes to precipitate the product. The resulting slurry was then stirred for 1 hour and filtered. The solids were washed with water (4 mL) and then dried in the oven to afford Compound I-1 as a static-laden, light green powder (343 mg, 93%). $^1$H NMR (400 MHz, DMSO-$d_6$) δ ppm 7.74 (s, 1H) 7.72 (d, J=2.34 Hz, 1H), 7.49 (dd, J=8.79, 2.54 Hz, 1H), 7.29 (d, J=8.59 Hz, 1H), 7.02 (d, J=7.81 Hz, 2H), 5.95 (d, J=8.20 Hz, 1H), 5.24 (d, J=14.06 Hz, 1H), 5.13 (d, J=14.06 Hz, 1H), 4.68 (quin, J=6.93 Hz, 1H), 3.31 (br s, 1H), 2.52 (s, 4H), 2.19 (s, 3H), 1.48 (d, J=6.64 Hz, 3H). LCMS: (ESI) m/z 399 [M−H]. LCMS data for Compound (I-1) indicated a molecular ion of $[M+1]^+$=401, and a fragment peak of m/z 206.

Compositions comprising both Compound 1-1 and Compound 1-2 were prepared. In one composition, the mother liquors collected from the crystallization of Compound I-2 were concentrated, and then enriched with Compound 1-1 to a level of 0.61% a/a. A portion of this enriched batch was purified by preparative HPLC, and LCMS and $^1$H NMR data were collected. The characterization data for the enriched batch were consistent with what was expected from a composition of Compound 1-2 enriched with Compound I-1.

In other compositions comprising Compound I-2, Compound I-1 was present at levels of 0.20% a/a, 0.05% a/a and 0.45% a/a, measured by HPLC.

Example 2. IDH1-R132H and IDH1-R132C Enzymatic Assay

Assays were performed in a 384-well black plate. An aliquot of 250 nL of compound was incubated with 10 μL of 30 nM IDH1-R132H or 10 nM IDH1-R132C recombinant protein in assay buffer (50 mM Tris pH=7.5, 150 mM NaCl, 5 mM $MgCl_2$, 0.1% (w/v) Bovine Serum Albumin, and 0.01% Triton X-100) in each well at 25° C. for 15 minutes. After the plate was centrifuged briefly, an aliquot of 10 μL of 2 mM α-ketoglutarate and 20 μM NADPH solution prepared in assay buffer was then added to each well and the reaction was maintained at 25° C. for 45 minutes. An aliquot of 10 μL of diaphorase solution (0.15 U/mL diaphorase and 30 μM Resazurin in assay buffer) was added to each well. The plate was maintained at 25° C. for 15 minutes and then read on a plate reader with excitation and emission wavelengths at 535 nm and 590 nm, respectively. The $IC_{50}$ of a given compound was calculated by fitting the dose response curve of inhibition of NADPH consumption at a given concentration with a four parameter logistic equation.

We claim:
1. A Compound I-1 or pharmaceutically acceptable salt thereof:

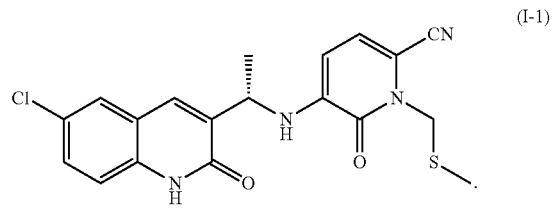 [SMILES: CSCn1c(C#N)ccc(N[C@@H](C)c2cc3cc(Cl)ccc3[nH]c2=O)c1=O]

2. A pharmaceutical composition comprising the compound of claim 1.
3. The pharmaceutical composition of claim 2, further comprising Compound I-2 or a pharmaceutically acceptable salt thereof:

(I-2)

4. The pharmaceutical composition of claim 3, comprising a total of 0.01-0.5% (a/a HPLC) Compound I-1, relative to Compound I-2.
5. The pharmaceutical composition of claim 3, comprising up to about 1.33 mg of Compound I-1 per 300 mg of Compound I-2.
6. A unit dosage form indicated for oral administration comprising the pharmaceutical composition of claim 4.
7. The unit dosage form of claim 6, wherein the unit dosage form is a capsule or tablet comprising 50 mg or 150 mg of Compound I-2.
8. A unit dosage form indicated for oral administration comprising the pharmaceutical composition of claim 5.
9. The unit dosage form of claim 8, wherein the unit dosage form is a capsule or tablet comprising 50 mg or 150 mg of Compound I-2.
10. A method of inhibiting mutant isocitrate dehydrogenase 1 (mIDH1) comprising contacting the compound of claim 1 with a cell harboring an IDH1 mutation selected from the group consisting of R132H and R132C.
11. A method of treating a patient diagnosed with acute myeloid leukemia (AML) harboring an IDH1 mutation, the method comprising administering to the patient in need thereof a therapeutically effective amount of the pharmaceutical composition of claim 3.
12. The method of claim 11, comprising administering to the patient up to about 22 mg of Compound I-1 per day.
13. The method of claim 12, comprising administering to the patient up to about 1.33 mg of Compound I-1 per day.
14. The method of claim 13, comprising orally administering 150 mg of Compound I-2 to the patient twice a day.
15. A method of treating a patient diagnosed with a glioma harboring an IDH1 mutation, the method comprising administering to the patient in need thereof a therapeutically effective amount of the pharmaceutical composition of claim 3.

16. The method of claim 15, comprising administering to the patient up to about 22 mg of Compound I-1 per day.

17. The method of claim 16, comprising administering to the patient up to about 1.33 mg of Compound I-1 per day.

18. The method of claim 17, comprising orally administering 150 mg of Compound I-2 to the patient twice a day.

19. The method of claim 15, further comprising administering azacitidine to the patient.

20. The method of claim 19, wherein the pharmaceutical composition is administered to the patient during one or more 28-day treatment cycles, wherein:
   (a) the azacitidine is administered intravenously or subcutaneously to the patient in a dose of 75 mg/m$^2$ for 7 days per every 28-day treatment cycle; and
   (b) 150 mg of Compound I-2 is administered twice daily to the patient every day throughout the one or more 28-day treatment cycles.

\* \* \* \* \*